United States Patent [19]

Clayton

[11] 4,129,643
[45] Dec. 12, 1978

[54] METHOD FOR RAPID SCREENING OF TERATOGENIC AGENTS

[76] Inventor: Ruth M. Clayton, 1, Seton Pl., Edinburgh 9, Scotland

[21] Appl. No.: 812,176

[22] Filed: Jul. 1, 1977

[30] Foreign Application Priority Data

Jul. 15, 1976 [GB] United Kingdom ................. 1546/76

[51] Int. Cl.² ....................... A61K 29/00; A61K 43/00
[52] U.S. Cl. ....................................... 424/1; 23/230.3; 195/1.7; 424/9
[58] Field of Search ................. 424/1, 1.5, 9; 195/1.7, 195/1.8, 120; 23/230.3

[56] References Cited

PUBLICATIONS

Shemada, Med. Pharm., vol. 10, No. 5, 1976, pp. 186–189.
McElhatt, B. J., Pharm., vol. 59, No. 3, 1977, pp. 494–495.
Gabka, Med. Klin., vol. 72, No. 1, 1977, pp. 31–32.

Primary Examiner—Benjamin R. Padgett
Assistant Examiner—Christine M. Nucker
Attorney, Agent, or Firm—Michael J. Striker

[57] ABSTRACT

The invention relates to a process for screening a compound for teratogenic activity which comprises administering the compound to a test animal and using amniotic fluid from the test animal in a cell culture medium. The compound tested is screened on the basis of cell growth in the culture medium.

7 Claims, No Drawings

METHOD FOR RAPID SCREENING OF TERATOGENIC AGENTS

The present invention relates to a novel method of screening substances including drugs, environmental pollutants and other substances with potential effects on biological systems for their possible deleterious effects on the development and normality of the mammalian foetus including the human foetus after exposure of the maternal organism to the substance in question.

BACKGROUND

Current tests of new drugs and other agencies for possible teratogenic effects on the human foetus are slow and expensive. Such tests are generally performed by the examination of some thousand rodent foetuses of various ages from pregnant females injected or fed with suspected teratogenic substances at different stages of pregnancy and at different dose levels. Other mammals are sometimes used. The embryos are examined for morphopathology and for hisopathology. Different periods of foetal sensitivity and different levels of susceptibility between strains and species characterise the response to teratogenic agencies. For this reason some investigations have used more than one species. Nevertheless the applicability of tests on rodents etc. to effects expected in man must always remain in doubt, since there are differences in placental structure and physiology as well as pharmacogenetic differences between species, yet tests on primates are even more expensive and time consuming than rodent tests, and are therefore not often undertaken.

The costs to industry (excluding all overheads) even in 1975 were of the order of several thousands of pounds per substance tested in such a way. Each substance requires about a year of laboratory time. It is understandable therefore that information regarding teratogenicity sometimes remains to be deduced from epidemiological studies of human populations, after some family tragedies have already occurred.

Since the number of potentially teratogenic substances increases faster than the capacity for testing by methods using intact animals, alternative forms of screening have been considered by several authors including organ or cell culture systems in vitro. However, three fundamental problems remain.

A very serious problem is the form in which the substance should be presented to the cultures, since some substances administered to the mother in vivo do not exert their teratogenic effect directly on the foetus, but through a toxic or persistent metabolite: and may be harmless in vitro. Conversely, a substance toxic in vitro may be metabolished rapidly to a harmless agent in vivo. Furthermore, relevant dose levels for a particular group of susceptible cells may not be related in any obvious way to the dose administered in vivo.

The method of scoring of effect presents a problem, since organ cultures require histological investigations and growth measurements which are very time-consuming, while cell cultures are difficult to score objectively, except for cytotoxic effects which are frequently associated with non-physiological levels of substances in the medium. Therefore, the method of scoring of results must exclude cytotoxicity if it is to be discriminating or morphology of the cells if it is to be objective A suitably responsive test cell system is required.
The method A procedure is described below which avoids these problems. It is also inexpensive (less than $f100$ per substance tested at 1975 prices) and is rapid, objective, discriminant and data obtained from the use of non-primate material is capable of being confirmed by using primate (e.g. human) cells where indicated. It may also, in principle, be applicable to very small amounts of human foetal tissue (by-passing, if necessary, tests on non-primate systems).

According to my invention I provide a process for screening a compound for teratogenic activity comprising administering the compound being screened to a test animal, removing amniotic fluid from the test animal, using the amniotic fluid removed as part or all of a cell culture medium, and measuring the effect on cell properties of cells grown in the culture medium containing the amniotic fluid from the test animal as compared with the use of amniotic fluid from an otherwise identical control animal that has not had the compound being screened administered to it.

In more detail, in its generally preferred aspect, the procedure I have devised and tested is as follows:

(1) Amniotic fluid is used as cell culture medium or as an additive to a standardised cell culture medium in order to test the substance as processed by the maternal organism. Amniotic fluids either from animals of diverse genotype or of selected genotypes, as required, are pooled. Controls are provided by amniotic fluids from uninjected/ untreated/unexposed individuals and the assays are provided by amniotic fluids from individuals exposed, injected or otherwise treated withbthe substances to be tested. Amniotic fluid is harvested shortly after exposure to the agent (e.g. 1-2 hours after administration or according to the rate of uptake).

The substance tested is thus presented to the cells in the form and at the dose to which the foetus would be exposed, and problems due to different periods of feotal sensitivity are also bypassed.

(2) A standardised cell suspension is innoculated into cultures and grown during log phase in the medium containing amniotic fluid from a control or test series as described above. Foetal cells are normally used but cells from embryonic or other stages may be used instead where appropriate. Cells in lag or confluent phase may be exposed where appropriate. Cells are labelled for a short period (not more than a few hours) before being harvested, with C14 amino acids. A cell system is required which is sensitive to changes in metabolism while remaining viable. Lens epithelium has been used since I have published evidence that quantitative regulation of specific syntheses is of especial importance in this orgen and the assay system described in (3) below detects changes in mitotic rate, cell mass, and growth conditions, cell surface modification and genetically determined pathology.

However, since it is possible that some substances may be found to which this tissue system is not sensitive, other cell culture systems such as fibroblasts, neural cells, endothelial or epithelial cells, etc. may be used instead of lens epithelium and are preferably used in addition to it for a fuller battery of tests.

(3) An assay method which is rapid, repeatable, objective and quantitative is provided by the measurement of the profiles of accumulation and synthesis of individual proteins of the test cells (the synthesis being measured after incorporation of radioactive precursors before harvesting), as demonstrated by the densitometric quantitation (using any suitable accurate commercial densitometer) of the cell contents after resolution by high-resolution separation, e.g. by isoelectric focussing in polyacrylamide gels or other stabilising media in dissociating conditions (e.g. by using 6-8M urea) and staining with any of the quantitative protein stains (or in principle by absorbance at appropriate wavelength with unstained material). Similar densitometry is made of the autoradiograph of the gels. Each analysis can be done on a culture grown from a cell suspension of as little as $1-4.5 \times 10^5$ cells, but can be scaled up or down as required.

Cell contents for analysis may be extracted by any standard procedure such as freezing and thawing, sonication, homogenisation etc.

This procedure has been found, in tests on two teratogens in the mouse (6 aminonicotinamide and salicylate), to distinguish reliably and specifically between the cells treated by each of these teratogens, and control cells. It has also been used successfully on methadone-hydrochloride, methanol, corticesteroids and antihistamines in a pilot study. The method can be adopted for use in a primate system for further testing of any substances giving cause for concern (primate includes human).

The test has also correctly detected the teratogenic compound from two coded compounds of unknown nature which were supplied for test by a pharmaceutical investigator from a major drug company. Using a panel of four foetal cell types the nature of the defects of exposed foetuses was also correctly deduced. The non-teratogenic compound was the one found harmless by this test.

Time usually required for one assay, 11-15 days. However, by using fluorography, according to Bonner and Lasky, 1974, (European Journal of Biochemistry, 46, 83-88) instead of autoradiography the test may be completed in 9-10 days.

The following Example illustrates the invention.

EXAMPLE

Amniotic fluid

Mice of numerous genotypes were taken from amongst all the more prolific strains available from the Institute of Animal Genetics Mouse House (Mouse News Letter, 1974). They were mated and the pregnancies dated by vaginal plug. They were injected once, subcutaneously, with a teratogen, between 12-15 days of gestation in order to obtain a large volume of clear amniotic fluid. 1-2 hours after the injection the mice were killed by cervical dislocation, the uteri removed and the amniotic fluid harvested under sterile conditions, passed through a Millex filter and stored at −20°C. Control amniotic fluids were obtained from uninjected mice of a similar range of genotypes and stages of gestation. Mice were injected with double the teratogenic doses used for 6-aminonicotinamide by Pinsky and Fraser (Biol. Neonat., 1,106-112 (1959)) and for sodium acetyl salicylate by Larsson and Erickson (Acta. Paed. Scand., 55, 569-576, )1976)), but the amniotic fluids were diluted to 50% with culture medium for use, thus giving a final concentration similar to that used by these authors. Five batches of pooled amniotic fluid of each kind were prepared in this way and tested in separate culture experiments.

Tissue culture

Cultures of dissociated lens epithelial cells were prepared according to Okada, Eguchi and Takeichi (Dev. Growth Diffn., 13,323-326 (1971)), and plated at $4.5 \times 10^5$ cells per dish in 3.5 ml Earles MEM (Biocult) containing 6% foetal calf serum (Gibco). The medium was changed at 2 days, and after 4 days, when these cells were in log phase, the medium was replaced by 1 ml of medium and 1 ml of amniotic fluid. After two further days the cells were labelled for 4 to 5 hours with $^{14}C$ mixed amino acids (Amersham) at 20 $\mu$Ci/ml. The cultures were washed several times in Hanks solution, harvested with a miniature plastic scraper and taken up into a drop of 8M urea containing 10 mM $\beta$-mercaptoethanol. The drop was frozen and thawed three times to liberate the cell contents. When required, the living cells were examined with a Gilbert and Siebert inverted phase microscope.

Analysis of Protein Content

Polyacrylamide gels containing ampholines according to Wrigley (Science Tools, 15, 17-23, (1968)) were modified to contain 6M urea, 10mM $\beta$-mercaptoethanol, and an ampholine mixture giving a gradient from pH 3 to 10, flattened in the region of 4.5 to 7.0. Such gels give especially high resolution for crystallins and are now routinely used in my laboratory. 20 $\mu$l of cell preparation was added to each gel which was electrofocussed overnight according to Wrigley (loc. cit.). Gels were stained in Coomassie Blue, scanned with a Joyce-Loebl densitometer, sliced longitudinally, dried down onto Whatman No. 3 paper, in a modification of the method of Daniel and Wild (Anal. Biochem, 35, 544-545, (1970)) and clamped to a sheet of X-ray film. After 4 to 5 days of exposure the autoradiograph was developed and scanned. The entire procedure, from cell culture to final scan, was completed in 11-12 days.

Results

The protein profile of the lens epithelial cells grown in medium containing amniotic fluid is the same as that in medium without amniotic fluid. Cells grown in amniotic fluid from mice injected with 6-aminonicotinamide had a modified cell outline and a consistent set of changes in the protein profile, one band being missing and one exaggerated; while some other, less striking quantitative changes were also recorded. A few were probably no greater than random fluctuations, but many were seen regularly. Cells grown in amniotic fluid from mice injected with sodium acetyl salicylate are normal in morphology (unless they and their controls are grown in sub-optimal conditions). In all cases they were lacking in the band which was enhanced by 6-aminonicotinamide treatment. Other quantitative changes were also observed. Quantitative changes in the autoradiograph traces were found which distinguish equally well between the effects of these two drugs. Changes in the stained gels indicate changes in accumulated protein, those in the autoradiographs, changes in protein synthesis. These changes are presumably related to each other.

What is claimed is:

1. A process for screening a compound for teratogenic activity comprising administering the compound being screened to a test animal, removing amniotic fluid from the test animal, using the amniotic fluid removed as at least part of a cell culture medium, and measuring the effect on cell properties of cells grown in the culture medium containing the amniotic fluid from the test animal as compared with the use of amniotic fluid from an otherwise identical control animal that has not had the compound being screened administered to it.

2. A process as claimed in claim 1 wherein the amniotic fluid is used as at least part of the culture medium for the culturing of lens epithalium cells.

3. A process as claimed in claim 1 wherein foetal cells are used.

4. A process as claimed in claim 1 wherein the profiles of accumulation and synthesis of individual proteins of the cells being cultured are measured, the synthesis being measured after incorporation of radioactive precursor before harvesting.

5. A process as claimed in claim 4 wherein said measurement is carried out by densitometric quantitation of the cell contents after resolution by high-resolution separation.

6. A process as claimed in claim 5 wherein the high-resolution separation is performed by isoelectric focussing in a stabilising medium in dissociating conditions and staining with a quantitative protein stain.

7. A process as claimed in claim 5 wherein the densitometric quantitation is performed after autoradiography or fluorography of the proteins resolved by the high-resolution separation.

* * * * *